United States Patent
Grant et al.

(10) Patent No.: US 7,598,276 B2
(45) Date of Patent: Oct. 6, 2009

(54) PHARMACEUTICAL SALTS AND POLYMORPHS OF A FACTOR XA INHIBITOR

(75) Inventors: Craig Grant, Burwell (GB); James P. Kanter, San Ramon, CA (US); Graeme Langlands, Soham (GB)

(73) Assignee: Millenium Pharmaceuticals, Inc., Cambridge, MA (US)

( * ) Notice: Subject to any disclaimer, the term of this patent is extended or adjusted under 35 U.S.C. 154(b) by 1 day.

(21) Appl. No.: 11/594,280

(22) Filed: Nov. 7, 2006

(65) Prior Publication Data

US 2007/0112039 A1    May 17, 2007

Related U.S. Application Data

(60) Provisional application No. 60/735,224, filed on Nov. 8, 2005.

(51) Int. Cl.
A61K 31/44 (2006.01)
C07D 213/53 (2006.01)

(52) U.S. Cl. ..................... 514/352; 546/309
(58) Field of Classification Search .............. 546/309; 514/352
See application file for complete search history.

(56) References Cited

U.S. PATENT DOCUMENTS

| | | | |
|---|---|---|---|
| 6,376,515 B2 | 4/2002 | Zhu et al. | |
| 6,627,646 B2 * | 9/2003 | Bakale et al. | 514/322 |
| 6,835,739 B2 | 12/2004 | Zhu et al. | |
| 6,844,367 B1 | 1/2005 | Zhu et al. | |
| 2005/0261346 A1 | 11/2005 | Zhu et al. | |
| 2006/0020039 A1 | 1/2006 | Zhu et al. | |
| 2006/0241153 A1 | 10/2006 | Zhu et al. | |
| 2007/0021472 A1 | 1/2007 | Zhu et al. | |

OTHER PUBLICATIONS

CMU Pharmacuetical polymorphism, internet p. 1-3 (2002) (printout Apr. 3, 2008).*
Singhal et al., :"Drug polymorphism, etc.," Advanced drug delivery reviews 56, p. 335-347 (2004).*
Rowland et al., "Clinical Pharmacokinetics, etc.," 1996, p. 123.*
Silverman, The Organic Chemistry of Drug Design and Drug Action, NY: Academic Press, 1993, 72-76.*
Doelker, english translation of Ann. Pharm. Fr. 2002, 60: 161-176, pp. 1-39.*
Doelker, english translation of S.T.P. Pharma Pratiques (1999), 9(5), 399-409, pp. 1-33.*
Brittain et al., Polymorphism in Pharamceutical Solids, NY: Marcel Dekker, INc., 1999, pp. 1-2, 183-226.*
Muzaffer et al. J of Pharmacy (Lahore) 1979, 9(1), pp. 59-66.*
Tadayet al., J of Pharmaceutical Sciences, 92(4), 2003, pp. 831-838.*
Chemical & Engineering News, Feb. 2003, pp. 32-35.*
U.S. Pharmacopia #23, National Formulary #18 (1995) 1843-1844.*
Concise Encyclopedia Chemistry, NY: Walter de Gruyter Berlin 1994, 872-873.*
Jain et al. Polymorphism in Pharmacy, Indian Drugs, 1986, 23(6), pp. 315-329.*
Otsuka et al. Chem. Pharm. Bull. 47(6), 1999, pp. 852-856.*

* cited by examiner

*Primary Examiner*—Patricia L Morris
(74) *Attorney, Agent, or Firm*—Swiss Tanner, P.C.

(57) ABSTRACT

The present invention provides for salts comprising a compound of Formula I and an acid that has activity against mammalian factor Xa. The present invention is also directed to methods of making the compound of Formula I.

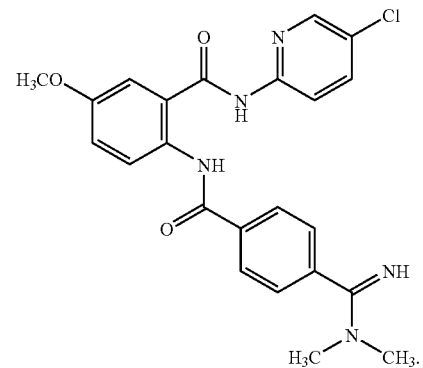

5 Claims, 5 Drawing Sheets

DSC and TGA of the compound of Formula II

Views of the compound of Formula II from crystal structure data

PHARMACEUTICAL SALTS AND POLYMORPHS OF A FACTOR XA INHIBITOR

CROSS-REFERENCES TO RELATED APPLICATIONS

This application claims the benefit under 35 U.S.C. § 119(e) of U.S. Provisional Application Ser. No. 60/735,224 filed Nov. 8, 2005, which is hereby incorporated by reference in its entirety.

BACKGROUND OF THE INVENTION

1. Field of the Invention

This invention is directed to novel salts of a factor Xa inhibitor, polymorphs thereof and methods of making the factor Xa inhibitor.

2. State of the Art

Hemostasis, the control of bleeding, occurs by surgical means, or by the physiological properties of vasoconstriction and coagulation. This invention is particularly concerned with blood coagulation and ways in which it assists in maintaining the integrity of mammalian circulation after injury, inflammation, disease, congenital defect, dysfunction, or other disruption. Although platelets and blood coagulation are both involved in restoring hemostasis and in thrombotic diseases, certain components of the coagulation cascade are primarily responsible for the amplification and acceleration of the processes involved in platelet aggregation and fibrin deposition which are major events in thrombosis and hemostasis.

Clot formation involves the conversion of fibrinogen to fibrin which polymerizes into a network to restore hemostasis after injury. A similar process results in occluded blood vessels in thrombotic diseases. The conversion of fibrinogen to fibrin is catalyzed by thrombin, the end product of a series of reactions in the blood coagulation cascade. Thrombin is also a key player in activating platelets, thereby contributing to thrombosis under conditions of both arterial and venous blood flow. For these reasons, it has been postulated that efficient regulation of thrombin can lead to efficient regulation of thrombosis. Several classes of currently used anticoagulants directly or indirectly affect thrombin (i.e. unfractionated heparins, low-molecular weight heparins, heparin-like compounds, pentasaccharide and warfarin). Direct or indirect inhibition of thrombin activity has also been the focus of a variety of anticoagulants in clinical development (reviewed by Eriksson and Quinlan, *Drugs* 11: 1411-1429, 2006).

Prothrombin, the precursor for thrombin, is converted to the active enzyme by factor Xa. Localized activation of tissue factor/factor VIIa mediated factor Xa generation is amplified by the factor IXa/factor VIIIa complex and leads to prothrombinase assembly on activated platelets. Factor Xa, as a part of the prothrombinase complex, is the sole enzyme responsible for sustained thrombin formation in the vasculature. Factor Xa is a serine protease, the activated form of its precursor Factor X, and a member of the calcium ion binding, gamma carboxyglutamic acid (GLA)-containing, vitamin K dependent, and blood coagulation factors. Unlike thrombin, which acts on a variety of protein substrates including fibrinogen and the PAR receptors (Protease activated receptors, Coughlin, *J. Thrombosis Haemostasis* 3: 1800-1814, 2005), factor Xa appears to have a single physiologic substrate, namely prothrombin. Since one molecule of factor Xa may be able to generate greater than 1000 molecules of thrombin (Mann, et al., *J. Thrombosis. Haemostasis* 1: 1504-1514, 2003), direct inhibition of factor Xa as a way of indirectly inhibiting the formation of thrombin may be an efficient anticoagulant strategy. This assertion is based on the key role of prothrombinase in thrombin synthesis and on the fact that inhibition of prothrombinase will have a pronounced effect on the overall platelet aggregation and clotting pathways.

Activated proteases such as factor VIIa, factor IXa or factor Xa have poor proteolytic activity on their own. However, their assembly into cofactor-dependent, membrane-bound complexes significantly enhances their catalytic efficiencies. This effect is most dramatic for factor Xa, where the efficiency is increased by a factor of $10^5$ (Mann, et al., *Blood* 76(1):1-16, 1990). Due to the higher concentration of the zymogens present in blood (1.4 µM prothrombin versus 150 nM factor Xa) and the kinetics of activation, a smaller amount of factor Xa than thrombin needs to be inhibited to achieve an anticoagulant effect. Indirect proof of the hypothesis of superiority of factor Xa as a therapeutic target compared to thrombin can also be found in clinical trials for the prevention of deep vein thrombosis. Fondaparinux, an antithrombin III dependent factor Xa inhibitor, was proven to be superior to enoxaparin (a low molecular weight heparin that inhibits both thrombin and factor Xa) in four trials of orthopedic surgery (Turpie, et al., *Archives Internal Medicine* 162(16): 1833-1840, 2002). Therefore, it has been suggested that compounds which selectively inhibit factor Xa may be useful as in vitro diagnostic agents, or for therapeutic administration in certain thrombotic disorders, see e.g., WO 94/13693.

Several factor Xa inhibitors have been reported as polypeptides derived from hematophagous organisms, as well as compounds which are not large polypeptide-type inhibitors. Additional factor Xa inhibitors include small molecule organic compounds, such as nitrogen containing heterocyclic compounds which have amidino substituent groups, wherein two functional groups of the compounds can bind to factor Xa at two of its active sites. For example, WO 98/28269 describes pyrazole compounds having a terminal amidino (—C(=NH)—NH$_2$) group; WO 97/21437 describes benzimidazole compounds substituted by a basic radical which are connected to a naphthyl group via a straight or branched chain alkylene, —C(=O)— or —S(=O)$_2$— bridging group; WO 99/10316 describes compounds having a 4-phenyl-N-alkylamidino-piperidine and 4-phenoxy-N-alkylamidino-piperidine group connected to a 3-amidinophenyl group via a carboxamidealkyleneamino bridge; and EP 798295 describes compounds having a 4-phenoxy-N-alkylamidino-piperidine group connected to an amidinonaphthyl group via a substituted or unsubstituted sulfonamide or carboxamide bridging group.

Additional reported factor Xa inhibitors include those having a structure comprising a phenyl-amidino, phenyl, and halo-phenyl connected via amide linkages (U.S. Pat. No. 6,844,367 B1). Other factor Xa inhibitors have replaced the halo-phenyl with a halo-pyridyl (see U.S. Pat. Nos. 6,376,515 B2 and 6,835,739 B2). U.S. Pat. No. 6,376,515 B2 discloses a specific factor Xa inhibitor compound identified in Example 206, which is also disclosed in U.S. Pat. No. 6,835,739 B2 as Example 206 and herein identified as a compound of Formula I. The compound of Formula I is represented by the structure:

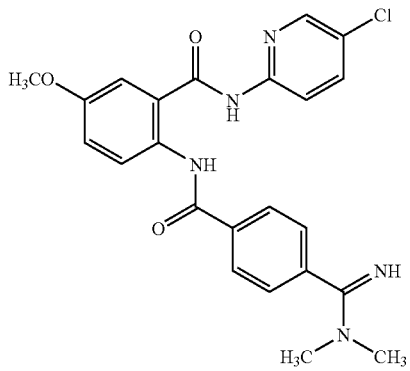

Further work in developing selective inhibitors of factor Xa has led to the surprising discovery that certain salts of this compound exhibit better thermal and hydrolytic stability than the free-base compounds themselves or other salts, with the maleate salt having the best stability observed.

SUMMARY OF THE INVENTION

In one embodiment, the invention is directed to a salt comprising a compound Formula I:

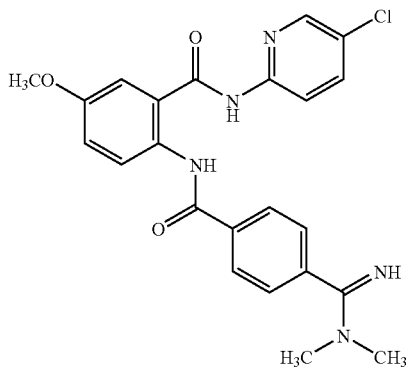

and an acid, wherein the acid is selected from the group consisting of hydrochloric, lactic, maleic, phenoxyacetic, propionic, succinic, adipic, ascorbic, camphoric, gluconic, phosphic, tartric, citric, methanesulfonic, fumaric, glycolic, naphthalene-1,5-disulfonic, gentisic and benzenesulfonic.

In a preferred embodiment, the acid is selected from the group consisting of hydrochloric, lactic, maleic, phenoxyacetic, propionic, succinic, adipic, ascorbic, camphoric, gluconic, phosphic, tartric, citric, and methanesulfonic.

In another preferred embodiment, the acid is selected from the group consisting of hydrochloric, lactic, maleic, phenoxyacetic, propionic, and succinic. In one embodiment, the salt is the maleate salt or the propionate salt. It is contemplated that the maleate salt of the compound of Formula I could be formed by protonating one or more nitrogen atoms of the compound of Formula I. In one embodiment, the amidino nitrogen (=NH) of Formula I is protenated (=NH$_2^+$) to form the salt.

In one preferred embodiment, the maleate salt of the compound of Formula I is represented by Formula II:

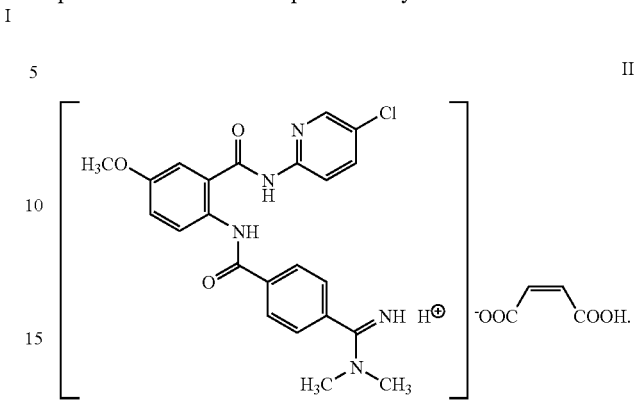

In another embodiment, the present invention provides a salt of Formula II having a crystalline polymorph form. In preferred embodiments, the crystalline polymorph form exhibits a powder X-ray diffraction pattern having at least four and more preferably eight of the following approximate characteristic peak locations: 4.9, 9.7, 13.8, 14.1, 15.2, 17.6, 18.5, 20.8, 21.6, 22.7, 24.1, 26.3, 26.8 degrees 2θ. In still another embodiment, the powder X-ray diffraction pattern has approximate characteristic peak locations of 4.9, 9.7, 11.8, 13.8, 14.1, 15.2, 17.6, 18.5, 19.9, 20.8, 21.6, 22.7, 24.1, 25.0, 26.3, 26.8 degrees 2θ. The invention contemplates that the approximate characteristic peaks will have a deviation of up to about ±0.2 degrees 2θ. In yet another embodiment, the powder X-ray diffraction pattern is approximate to the powder X-ray diffraction pattern shown in FIG. 1. In other embodiments, the present invention provides a salt of Formula II having a crystalline polymorph form having a differential scanning calorimetry pattern approximate to the differential scanning calorimetry pattern shown in FIG. 2. This crystalline polymorph of the salt of Formula II provides for a reproducible form of this compound suitable for clinical studies.

In a further embodiment, the present invention provides a pharmaceutical composition for preventing or treating a condition in a mammal characterized by undesired thrombosis comprising a pharmaceutically acceptable carrier and a therapeutically effective amount of a salt comprising the compound of Formula I, the maleate salt of the compound of Formula I, the salt of Formula II, or the salt of Formula II having a crystalline polymorph form. In another embodiment, the pharmaceutical composition is in tablet form. In yet another embodiment, the pharmaceutical composition is in capsule form. In still another embodiment, the pharmaceutical composition is in lozenge form. In other embodiments, the pharmaceutical composition is in a form suitable for infusion, injection, or transdermal delivery.

In some embodiments, the present invention provides a method for preventing or treating a condition in a mammal characterized by undesired thrombosis comprising administering to the mammal a therapeutically effective amount of a salt comprising the compound of Formula I, the maleate salt of the compound of Formula I, the salt of Formula II, or the salt of Formula II having a crystalline polymorph form. In another embodiment, the condition is selected from the group consisting of acute coronary syndrome, myocardial infarction, unstable angina, refractory angina, occlusive coronary thrombus occurring post-thrombolytic therapy or post-coronary angioplasty, a thrombotically mediated cerebrovascular syndrome, embolic stroke, thrombotic stroke, transient ischemic attacks, venous thrombosis, deep venous thrombosis, pulmonary embolus, coagulopathy, disseminated intravascular coagulation, thrombotic thrombocytopenic purpura, thromboanglitis obliterans, thrombotic disease associated with heparin-induced thrombocytopenia, thrombotic complications associated with extracorporeal circulation, thrombotic complications associated with instrumentation, and thrombotic complications associated with the fitting of prosthetic devices.

In another embodiment, the present invention provides a method for inhibiting the coagulation of a blood sample comprising the step of contacting the sample with a salt comprising the compound of Formula I, the maleate salt of the compound of Formula I, the salt of Formula II, or the salt of Formula II having a crystalline polymorph form.

In a further embodiment, the present invention provides a method of preparing a compound of Formula I comprising contacting $LiN(CH_3)_2$ with a compound of formula III:

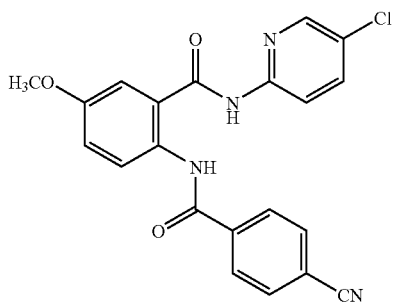

III or a salt thereof under conditions to form the compound of Formula I.

In some embodiments, the conditions are nucleophilic addition conditions and comprise use of a non-polar, aprotic solvent. In some other embodiments, the solvent is a member selected from the group consisting of tetrahydrofuran, diethyl ether, dimethoxymethane, dioxane, hexane, methyl tert-butyl ether, heptane, and cyclohexane. In some embodiments, the salt of the compound of Formula III is the HCl salt.

In some embodiments, the present invention provides a method of preparing a compound of Formula I wherein the method is performed at a temperature of less than 10° C.

In a further embodiment, the present invention provides a method of preparing a compound of Formula I wherein the compound having Formula I is afforded in a yield of at least 50%. In another embodiment, the compound having Formula I is afforded in a yield of at least 65%. In still another embodiment, the compound having Formula I is afforded in a yield of at least 75%.

In another embodiment, the present invention provides a method of making the compound of Formula I on a gram scale or a kilogram scale.

BRIEF DESCRIPTION OF THE DRAWINGS

FIG. 1A shows the observed diffraction pattern while FIG. 1B shows a calculated diffraction pattern.

DETAILED DESCRIPTION OF THE INVENTION

Figure 1A:
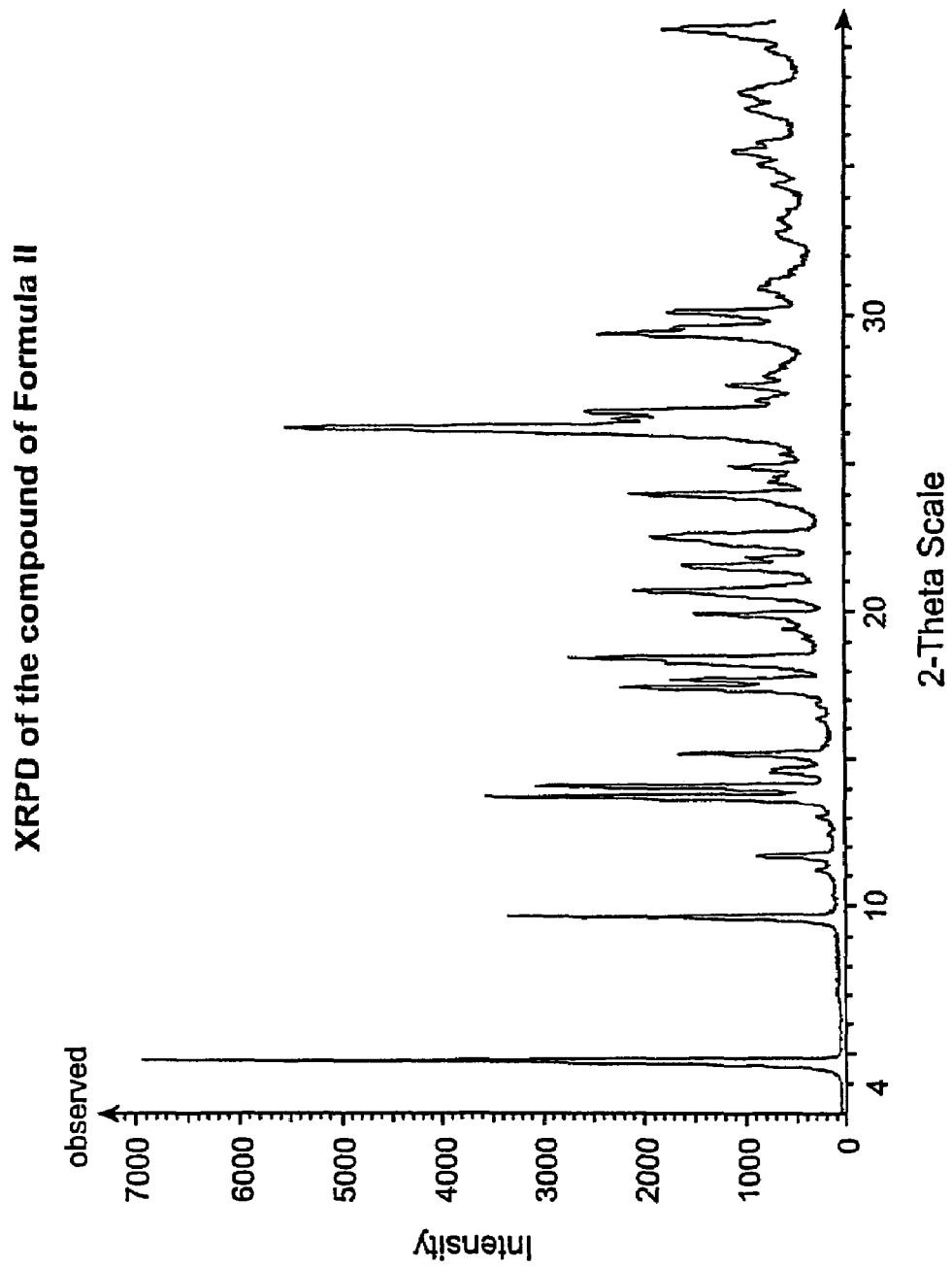
FIGS. 1A and 1B provide an X-ray powder diffraction (XRPD) of a form of Formula II (a maleate salt).

As discussed in U.S. Pat. No. 6,376,515 B2, a compound of Formula I is a potent factor Xa inhibitor. However, the compound of Formula I did not exhibit optimum solubility or crystallinity. The preparation of the acetate salt of the compound of Formula I was found to have good crystallinity, but did not possess good thermal and hydrolytic stability. Surprisingly and unexpectedly, it was found that certain salts show good crystallinity and thermal and hydrolytic stability, including; by way of example, HCl salt, lactate, maleate, phenoxyacetate, propionate, succinate, adipate, ascorbate, camphorate, gluconate, phosphate, tartrate, citrate, mesylate, fumarate, glycolate, naphthalene-1,5-disulphonate, gentisate and benzene sulfonate.

In particular, the maleate salt of Formula II exhibits excellent crystallinity, thermal and hydrolytic stability and purity. The maleate salt of Formula II of the present invention is useful for the treatment of undesired thrombosis in mammals.

I. Definitions

As used herein, the term "polymorph" refers to the crystalline form of a substance that is distinct from another crystalline form but that shares the same chemical formula.

The term "treatment" or "treating" means any treatment of a disease or disorder in a subject, such as a mammal, including:

preventing or protecting against the disease or disorder, that is, causing the clinical symptoms not to develop;

inhibiting the disease or disorder, that is, arresting or suppressing the development of clinical symptoms; and/or relieving the disease or disorder that is, causing the regression of clinical symptoms.

As used herein, the term "preventing" refers to the prophylactic treatment of a patient in need thereof. The prophylactic treatment can be accomplished by providing an appropriate dose of a therapeutic agent to a subject at risk of suffering from an ailment, thereby substantially averting onset of the ailment.

It will be understood by those skilled in the art that in human medicine, it is not always possible to distinguish between "preventing" and "suppressing" since the ultimate inductive event or events may be unknown, latent, or the patient is not ascertained until well after the occurrence of the event or events. Therefore, as used herein the term "prophylaxis" is intended as an element of "treatment" to encompass both "preventing" and "suppressing" as defined herein. The term "protection," as used herein, is meant to include "prophylaxis."

The term "therapeutically effective amount" refers to that amount of a salt of this invention, typically delivered as a pharmaceutical composition, that is sufficient to effect treatment, as defined herein, when administered to a subject in need of such treatment. The therapeutically effective amount will vary depending upon the subject and disease condition being treated, the weight and age of the subject, the severity of the disease condition, the particular compound chosen, the dosing regimen to be followed, timing of administration, the manner of administration and the like, all of which can be determined readily by one of ordinary skill in the art.

As used herein, the term "condition" refers to a disease state for which the compounds, salts, compositions and methods of the present invention are being used against.

As used herein, the term "blood sample" refers to whole blood taken from a subject, or any fractions of blood including plasma or serum.

II. Polymorphic Compounds

One embodiment of the invention is a salt comprising the compound of Formula I. One of skill in the art will appreciate that other salts of the free base of Formula I are also useful in the present invention. These other salts can be prepared using inorganic and organic acids which provide the requisite thermal and hydrolytic stability, such as, but not limited to, hydrochloric, lactic, maleic, phenoxyacetic, propionic, succinic, adipic, ascorbic, camphoric, gluconic, phosphic, tartric, citric, methanesulfonic, fumaric, glycolic, naphthalene-1,5-disulfonic, gentisic and benzenesulfonic. In one embodiment, the maleate salt of Formula II is represented as:

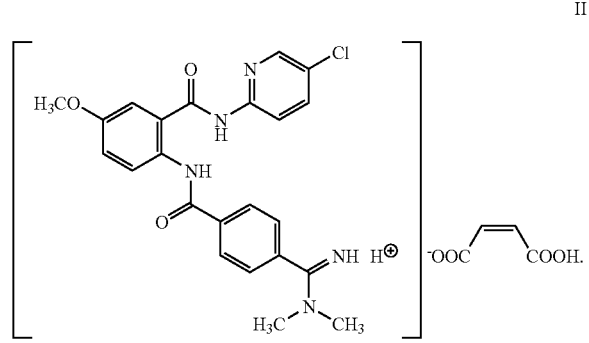

The salts of the present invention, such as the salt of Formula II, can adopt several different crystalline forms. The ability of a single compound to adopt one of many crystalline forms is termed polymorphism. A crystalline polymorph of a given compound is chemically identical to any other crystalline polymorph of that compound in containing the same atoms bonded to one another in the same way, but differs in its crystal forms. The different crystalline forms of the same compound can have an impact one or more physical properties, such as stability, solubility, melting point, bulk density, flow properties, bioavailability, etc.

Polymorphs can be characterized by their crystalline structure (X-ray diffraction pattern), their thermal properties (as determined by DSC and TGA), stability, solubility, etc. The X-ray diffraction pattern is presented as charasteristic peaks ±0.2 degrees 2θ. One polymorph of the salt of Formula II is characterized by the X-ray diffraction pattern shown in FIGS. 1A and 1B, the DSC/TGA data shown in FIGS. 2A and 2B, and the water sorption data shown in FIG. 3 or combinations of two of these characteristics or all of these characteristics. One of skill in the art will appreciate that other polymorphs of the salt of Formula II are also useful in the present invention.

III. Pharmaceutical Compositions

The pharmaceutical compositions of the present invention can be used for preventing or treating a subject suffering from a condition, wherein the condition is characterized by undesired thrombosis. The pharmaceutical compositions of the present invention are comprised of a pharmaceutically acceptable carrier and a therapeutically acceptable amount of a salt comprising the compound of Formula I, the maleate salt of the compound of Formula I, the salt of Formula II, or the salt of Formula II having a crystalline polymorph form.

A. Pharmaceutically Acceptable Carriers

Diagnostic applications of the salts of this invention will typically utilize formulations such as solutions or suspensions.

In the management of thrombotic disorders the salts of this invention may be utilized in compositions such as tablets, capsules, lozenges or elixirs for oral administration, suppositories, sterile solutions or suspensions or injectable administration, and the like, or incorporated into shaped articles. Subjects in need of treatment (typically mammalian subjects) can be administered appropriate dosages of the compounds of this invention that will provide optimal efficacy. The dose and method of administration will vary from subject to subject and be dependent upon such factors as the type of mammal being treated, its sex, weight, diet, concurrent medication, overall clinical condition, the particular salts employed, the specific use for which these salts are employed, and other factors which those skilled in the medical arts will recognize.

Capsules useful in the present invention can be prepared using conventional and known encapsulation techniques, such as that described in Stroud et al., U.S. Pat. No. 5,735,105. The capsule is typically a hollow shell of generally cylindrical shape having a diameter and length sufficient so that the pharmaceutical solution compositions containing the appropriate dose of the active agent fits inside the capsule. The exterior of the capsules can include plasticizer, water, gelatin, modified starches, gums, carrageenans, and mixtures thereof. Those skilled in the art will appreciate what compositions are suitable.

In addition to the active agent, tablets useful in the present invention can comprise fillers, binders, compression agents, lubricants, disintegrants, colorants, water, talc and other elements recognized by one of skill in the art. The tablets can be homogeneous with a single layer at the core, or have multiple layers in order to realize preferred release profiles. In some instances, the tablets of the instant invention may be coated, such as with an enteric coating. One of skill in the art will appreciate that other excipients are useful in the tablets of the present invention.

Lozenges useful in the present invention include an appropriate amount of the active agent as well as any fillers, binders, disintegrants, solvents, solubilizing agents, sweeteners, coloring agents and any other ingredients that one of skill in the art would appreciate is necessary. Lozenges of the present invention are designed to dissolve and release the active agent on contact with the mouth of the patient. One of skill in the art will appreciate that other delivery methods are useful in the present invention.

Formulations of the salts of this invention are prepared for storage or administration by mixing the salt having a desired degree of purity with physiologically acceptable carriers, excipients, stabilizers etc., and may be provided in sustained release or timed release formulations. Acceptable carriers or diluents for therapeutic use are well known in the pharmaceutical field, and are described, for example, in Remington's Pharmaceutical Sciences, Mack Publishing Co., (A. R. Gennaro Ed. 1985). Such materials are nontoxic to the recipients at the dosages and concentrations employed, and include buffers such as phosphate, citrate, acetate and other organic acid salts, antioxidants such as ascorbic acid, low molecular weight (less than about ten residues) peptides such as polyarginine, proteins, such as serum albumin, gelatin, or immunoglobulins, hydrophilic polymers such as polyvinylpyrrolidinone, amino acids such as glycine, glutamic acid, aspartic acid, or arginine, monosaccharides, disaccharides, and other carbohydrates including cellulose or its derivatives, glucose, mannose or dextrins, chelating agents such as EDTA, sugar alcohols such as mannitol or sorbitol, counterions such as sodium, and/or nonionic surfactants such as Tween, Pluronics or polyethyleneglycol.

Dosage formulations of the salts of this invention to be used for therapeutic administration must be sterile. Sterility is readily accomplished by filtration through sterile membranes such as 0.2 micron membranes, or by other conventional methods. Formulations typically will be stored in lyophilized form or as an aqueous solution. The pH of the preparations of this invention typically will be between 3 and 11, more preferably from 5 to 9 and most preferably from 7 to 8. It will be understood that use of certain of the foregoing excipients, carriers, or stabilizers will result in the formation of cyclic polypeptide salts. While the preferred route of administration is by injection, other methods of administration are also anticipated such as intravenously (bolus and/or infusion), subcutaneously, intramuscularly, colonically, rectally, nasally or intraperitoneally, employing a variety of dosage forms such as suppositories, implanted pellets or small cylinders, aerosols, oral dosage formulations (such as tablets, capsules and lozenges) and topical formulations such as ointments, drops and dermal patches. The sterile of this invention are desirably incorporated into shaped articles such as implants which may employ inert materials such as biodegradable polymers or synthetic silicones, for example, Silastic, silicone rubber or other polymers commercially available.

The salts of the invention may also be administered in the form of liposome delivery systems, such as small unilamellar vesicles, large unilamellar vesicles and multilamellar vesicles. Liposomes can be formed from a variety of lipids, such as cholesterol, stearylamine or phosphatidylcholines.

The salts of this invention may also be delivered by the use of antibodies, antibody fragments, growth factors, hormones, or other targeting moieties, to which the salt molecules are coupled. The salts of this invention may also be coupled with suitable polymers as targetable drug carriers. Such polymers can include polyvinylpyrrolidinone, pyran copolymer, polyhydroxy-propyl-methacrylamide-phenol, polyhydroxyethyl-aspartamide-phenol, or polyethyleneoxide-polylysine substituted with palmitoyl residues. Furthermore, salts of the invention may be coupled to a class of biodegradable polymers useful in achieving controlled release of a drug, for example polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels. Polymers and semipermeable polymer matrices may be formed into shaped articles, such as valves, stents, tubing, prostheses and the like.

B. Dosing

Typically, about 0.5 to 500 mg of a salt or mixture of salts of this invention is compounded with a physiologically acceptable vehicle, carrier, excipient, binder, preservative, stabilizer, dye, flavor etc., as called for by accepted pharmaceutical practice. The amount of active ingredient in these compositions is such that a suitable dosage in the range indicated is obtained.

It is contemplated that a typical dosage will range from about 0.001 mg/kg to about 1000 mg/kg, preferably from about 0.01 mg/kg to about 100 mg/kg, and more preferably from about 0.10 mg/kg to about 20 mg/kg. The compounds of this invention may be administered once or several times daily and other dosage regimens may also be useful.

IV. Methods

A. Preventing and Treating Disease Conditions Characterized by Undesired Thrombosis The salt of the present invention can be used for preventing or treating a condition in a mammal characterized by undesired thrombosis by administering to the mammal a therapeutically effective amount of a salt of the compound of Formula I, the maleate salt of the compound of Formula I, the salt of Formula II, or a salt of Formula II having a crystalline polymorph form. The salts can be used either alone or in conjunction with pharmaceutically acceptable excipients to prevent the onset of a condition characterized by undesired thrombosis. Prophylactic treatment can have substantial benefits for a patient at risk of an ailment, through decreased medical treatments and their associated mental and physical costs, as well as the direct monetary savings from avoiding prolonged treatment of a patient. For patients where the condition is not detected sufficiently early to prevent onset, the salt of the present invention can be used either alone or in conjunction with pharmaceutically acceptable excipients to treat the condition.

The preferred salts of the present invention are characterized by their ability to inhibit thrombus formation with acceptable effects on classical measures of coagulation parameters, platelets and platelet function, and acceptable levels of bleeding complications associated with their use while exhibiting suitable stability. Conditions characterized by undesired thrombosis would include those involving the arterial and venous vasculature.

With respect to the coronary arterial vasculature, abnormal thrombus formation characterizes the rupture of an established atherosclerotic plaque which is the major cause of acute myocardial infarction and unstable angina, as well as also characterizing the occlusive coronary thrombus formation resulting from either thrombolytic therapy or percutaneous transluminal coronary angioplasty (PTCA).

With respect to the venous vasculature, abnormal thrombus formation characterizes the condition observed in patients undergoing major surgery in the lower extremities or the abdominal area who often suffer from thrombus formation in the venous vasculature resulting in reduced blood flow to the affected extremity and a predisposition to pulmonary embolism. Abnormal thrombus formation further characterizes disseminated intravascular coagulopathy commonly occurs within both vascular systems during septic shock, certain viral infections and cancer, a condition wherein there is rapid consumption of coagulation factors and systemic coagulation which results in the formation of life-threatening thrombi occurring throughout the microvasculature leading to widespread organ failure.

The salts of the present invention, selected and used as disclosed herein, are believed to be useful for preventing or treating a condition characterized by undesired thrombosis, such as (a) the treatment of any thrombotically mediated acute coronary syndrome including myocardial infarction, unstable angina, refractory angina, occlusive coronary thrombus occurring post-thrombolytic therapy or post-coronary angioplasty, (b) the treatment of any thrombotically mediated cerebrovascular syndrome including embolic stroke, thrombotic stroke or transient ischemic attacks, (c) the treatment of any thrombotic syndrome occurring in the venous system including deep venous thrombosis or pulmonary embolus occurring either spontaneously or in the setting of malignancy, surgery or trauma, (d) the treatment of any coagulopathy including disseminated intravascular coagulation (including the setting of septic shock or other infection, surgery, pregnancy, trauma or malignancy and whether associated with multi-organ failure or not), thrombotic thrombocytopenic purpura, thromboangiitis obliterans, or thrombotic disease associated with heparin induced thrombocytopenia, (e) the treatment of thrombotic complications associated with extracorporeal circulation (e.g. renal dialysis, cardiopulmonary bypass or other oxygenation procedure, plasmapheresis), (f) the treatment of thrombotic complications associated with instrumentation (e.g. cardiac or other intravascular catheterization, intra-aortic balloon pump, coronary stent or cardiac valve), and (g) those involved with the fitting of prosthetic devices.

Accordingly, a method for treating a condition in a mammal characterized by undesired thrombosis comprises administering to the mammal a therapeutically effective amount of a salt of this invention. Disease states that are contemplated to be treatable using the salts of the present invention include, but are not limited to, acute coronary syndrome, myocardial infarction, unstable angina, refractory angina, occlusive coronary thrombus occurring post-thrombolytic therapy or post-coronary angioplasty, a thrombotically mediated cerebrovascular syndrome, embolic stroke, thrombotic stroke, transient ischemic attacks, venous thrombosis, deep venous thrombosis, pulmonary embolus, coagulopathy, disseminated intravascular coagulation, thrombotic thrombocytopenic purpura, thromboanglitis obliterans, thrombotic disease associated with heparin-induced thrombocytopenia, thrombotic complications associated with extracorporeal circulation, thrombotic complications associated with instrumentation, thrombotic complications associated with the fitting of prosthetic devices, occlusive coronary thrombus formation resulting from either thrombolytic therapy or percutaneous transluminal coronary angioplasty, thrombus formation in the venous vasculature, disseminated intravascular coagulopathy, a condition wherein there is rapid consumption of coagulation factors and systemic coagulation which results in the formation of life-threatening thrombi occurring throughout the microvasculature leading to widespread organ failure, hemorrhagic stroke, renal dialysis, blood oxygenation, and cardiac catheterization.

The maleate salt of the compound of Formula I or the salt of Formula II can also be used whenever inhibition of blood coagulation is required such as to prevent coagulation of stored whole blood and to prevent coagulation in other biological samples for testing or storage. Thus coagulation inhibitors of the present inhibition can be added to or contacted with stored whole blood and any medium containing or suspected of containing plasma coagulation factors and in which it is desired that blood coagulation be inhibited, e.g. when contacting the mammal's blood with material selected from the group consisting of vascular grafts, stents, orthopedic prosthesis, cardiac prosthesis, and extracorporeal circulation systems.

Besides being useful for human treatment, these salts are also contemplated to be useful for veterinary treatment of companion animals, exotic animals and farm animals, including mammals, rodents, and the like. More preferred animals include horses, dogs, and cats.

B. Administration

Therapeutic liquid formulations generally are placed into a container having a sterile access port, for example, an intravenous solution bag or vial having a stopper pierceable by hypodermic injection needle.

Therapeutically effective dosages may be determined by either in vitro or in vivo methods. For each particular salt of the present invention, individual determinations may be made to determine the optimal dosage required. The range of therapeutically effective dosages will be influenced by the route of administration, the therapeutic objectives and the condition of the patient. For injection by hypodermic needle, it may be assumed the dosage is delivered into the body's fluids. For other routes of administration, the absorption efficiency must be individually determined for each compound by methods well known in pharmacology. Accordingly, it may be necessary for the therapist to titer the dosage and modify the route of administration as required to obtain the optimal therapeutic effect. The determination of effective dosage levels, that is, the dosage levels necessary to achieve the desired result, will be readily determined by one skilled in the art. Typically, applications of the salts are commenced at lower dosage levels, with dosage levels being increased until the desired effect is achieved.

Typical adjuvants which may be incorporated into tablets, capsules, lozenges and the like are binders such as acacia, corn starch or gelatin, and excipients such as microcrystalline cellulose, disintegrating agents like corn starch or alginic acid, lubricants such as magnesium stearate, sweetening agents such as sucrose or lactose, or flavoring agents. When a dosage form is a capsule, in addition to the above materials it may also contain liquid carriers such as water, saline, or a fatty oil. Other materials of various types may be used as coatings or as modifiers of the physical form of the dosage unit. Sterile compositions for injection can be formulated according to conventional pharmaceutical practice. For example, dissolution or suspension of the active compound in a vehicle such as an oil or a synthetic fatty vehicle like ethyl oleate, or into a liposome may be desired. Buffers, preservatives, antioxidants and the like can be incorporated according to accepted pharmaceutical practice.

C. Combination Therapies

The salts of the present invention may also be used in combination with other therapeutic or diagnostic agents. In certain preferred embodiments, the salts of this invention may be coadministered along with other compounds typically prescribed for these conditions according to generally accepted medical practice such as anticoagulant agents, thrombolytic agents, or other antithrombotics, including platelet aggregation inhibitors, tissue plasminogen activators, urokinase, prourokinase, streptokinase, heparin, aspirin, or warfarin. The salts of the present invention may act in a synergistic fashion to prevent reocclusion following a successful thrombolytic therapy and/or reduce the time to reperfusion. These salts may also allow for reduced doses of the thrombolytic agents to be used and therefore minimize potential hemorrhagic side-effects. The salts of this invention can be utilized in vivo, ordinarily in mammals such as primates, humans, sheep, horses, cattle, pigs, dogs, cats, rats and mice, or in vitro.

D. Compound Preparation

1. The Maleate Salt of the Compound of Formula I

The compound of Formula I can be converted to salts of various inorganic and organic acids including, but not limited to, HCl salt, lactate, maleate, phenoxyacetate, propionate, succinate, adipate, ascorbate, camphorate, gluconate, phosphate, tartrate, citrate, mesylate, fumarate, glycolate, naphthalene-1,5-disulphonate, gentisate and benzene sulfonate. One of skill in the art will recognize that other acids can be used to make salts comprising the compound of Formula I that are useful in the present invention. It is also contemplated that salts of the invention can be readily converted to other salts of the invention.

To assess the thermal and hydrolytic stability of the salt, tests known to those of skill in the art are performed. These tests are more thoroughly discussed in Example 4 below.

A number of methods are useful for the preparation of the salts described above and are known to those skilled in the art. For example, reaction of the compound of Formula I with one or more molar equivalents of the desired acid in a solvent or solvent mixture in which the salt is insoluble, or in a solvent like water after which the solvent is removed by evaporation, distillation or freeze drying. Alternatively, the compound of Formula I may be passed over an ion exchange resin to form the desired salt or one salt form of the product may be converted to another using the same general process.

The compound of Formula I was prepared according to the procedure set forth below. The maleate salt of the compound of Formula I was chosen for its excellent crystallinity, thermal and hydrolytic stability, and high purity.

2. Formula I

The compound of Formula I can be prepared according to any of several different methodologies, either on a gram scale (<1 kg) or a kilogram scale (>1 kg). A gram-scale method is set forth below in Example 2. Another gram-scale method is set forth in U.S. Pat. No. 6,844,367B1, see Example 266, which is hereby incorporated by reference.

Alternatively, the compound of Formula I can be prepared on a kilogram scale using the procedure set forth in Example 2. The formation of the dimethyl amidine of Formula I involves nucleophilic attack on a cyano group by a deprotonated amine, with the deprotonated amine formed from a secondary amine and an alkyl lithium. As used herein, the term "alkyl" refers to a hydrocarbyl radical of from 1 to 8 carbon atoms. One of skill in the art will recognize that the deprotonated amine can be formed via other methods, and formation of the amidine functionality of Formula I can be prepared by a variety of other methods.

A useful solvent for the method of the present invention as described above is a non-polar, aprotic solvent such as tetrahydrofuran (THF), diethyl ether, dimethoxymethane, dioxane, hexane, methyl tert-butyl ether, heptane, and cyclohexane. In addition, the formation of the deprotonated amine can be carried at temperatures below 10° C. The nucleophilic addition of the amine to form the compound of Formula I can also be carried out at temperatures below 10° C. One of skill in the art will recognize that the methods of the present invention can be practiced using various other solvents, reagents, and reaction temperatures.

The compound of Formula I can be prepared using the method of the present invention in yields greater than 50%. In some instances, the compound of Formula I can be prepared in yields greater than 65%. In other instances, the compound of Formula I can be prepared in yields greater than 75%.

In addition while the method of the present invention for preparing the compound of Formula I on a gram-scale is similar to the procedure used on the kilogram-scale, there is an increase in the scale of the reaction of more than 3400%. Moreover, in several steps increased yields are obtained using reduced amounts of the excess reagents. One of skill in the art will recognize that the compound of Formula I can be prepared via other chemical methodologies on both a gram and kilogram scale.

V. EXAMPLES

Unless stated otherwise, the abbreviations used throughout the specification have the following meanings:
Å=Angstrom
A %=total percent area
aq.=aqueous
cm=centimeter
d=doublet
DSC=differential scanning calorimetry
EDTA=ethylenediaminetetraacetic acid
eq. equivalent
EtOH=ethanol
g=gram
HPLC=high performance liquid chromatography
hr=hour
Hz=Hertz
IR=infrared
J=coupling constant
kg=kilogram
kV=killivolts
L=liter
LOD=limit of detection
M=molar
m=multiplet
mA=milliampere
Me=methyl
MeO=methoxy
MeOH=methanol
mg=milligram
min.=minute
mL=milliliter
mm=millimeter
MTBE=methyl tert-butyl ether
N=normal
nM=nanomolar
NMR=nuclear magnetic resonance
s=singlet
TDS=total dissolved solids
TGA=thermal gravimetric analysis
THF=tetrahydrofuran
μM=micromolar Example 1

Preparation of a Crystalline Polymorph Salt of Formula II

Gram Scale Preparation

In a 3-necked 1500 mL round bottomed flash equipped with a condenser, free base compound of Formula I (25 g; 1 eq.) was charged and 9:1 EtOH/Water (500 mL) was added while stirring. The resulting slurry was heated to 70° C. Maleic acid (12.77 g; 2 eq.) was added dropwise as a solution (100 mL of 9:1 EtOH/Water) and after 50 mL had been added, the solution became noticeably clearer. On complete addition of the maleic acid solution, the temperature was held at 80° C. for 5 minutes. The vessel was allowed to cool slowly to 45° C. and 400 mL of MTBE was then added. The solution was stirred for 12 hr. The resulting precipitate was filtered and dried under vacuum. The salt of Formula II was recovered in a 45% yield (14.2 g).

Kilogram Scale Preparation

The compound of Formula I (24.6 Kg) was charged into a 760 L GLMS reactor (Reactor A). Maleic acid (12.7 Kg, 2.0 eq), ethanol (445 Kg, 18.1 parts), and high purity water (140 Kg, 5.7 parts) were added. The reaction mixture was adjusted to 22° C. (19 to 25° C.) and agitated at that temperature for ca. 1 hr, then transferred through a polishing filter into a conditioned 780 L Hastelloy reactor (Reactor B). The Reactor A pump and lines were rinsed forward into Reactor B with additional ethanol (ca. 45 Kg) via polishing filter. The filtrate was concentrated under vacuum with a maximum temperature of warm glycol bath (to heat reactor jacket) of 45° C., until ca. 140 L (5.7 parts volume) remained. The Reactor B contents were sampled for in-process NMR, which showed that mole ratio of ethanol:Formula II was 26. High purity water (49 Kg, 2.0 parts) was charged to Reactor B and concentration under vacuum resumed until a pot volume of ca.

140 L (5.7 parts volume) was achieved. In-process NMR indicated that the mole ratio of ethanol:salt of Formula II was 14. High purity water (49 Kg, 2.0 parts) was again charged and concentration under vacuum resumed to obtain a pot volume of ca. 140 L. In-process NMR showed that the mole ratio ethanol:salt of Formula II was 5. The temperature of the Reactor B contents were adjusted to 22° C. (19 to 25° C.) and formation of a slurry was visually confirmed. The reaction mixture was agitated at 22° C. (19 to 25° C.) for ca. 2 hrs, and then filtered onto a 30" centrifuge fitted with F-53 filter cloth. The Reactor B pump and lines were rinsed forward to the 30" centrifuge via polishing filter with two portions of high purity water (ca. 30 Kg each). The filter cake was sampled for in-process HPLC, which showed that the purity of the product was 99.1 A %, the largest impurity was 0.26 A %, and therefore recrystallization was unnecessary. The filter cake (33.1 Kg) was dried under vacuum with a maximum temperature of warm glycol bath (to heat reactor jacket) of 40° C. After ca. 30.5 hrs, in-process LOD analysis indicated a solvent content of 0%. The dry product was discharged (26.4 Kg) and stored at 2-8° C. The yield for the final product was slightly higher than expected at 85% (expected 50-80%).

Figure 1B:
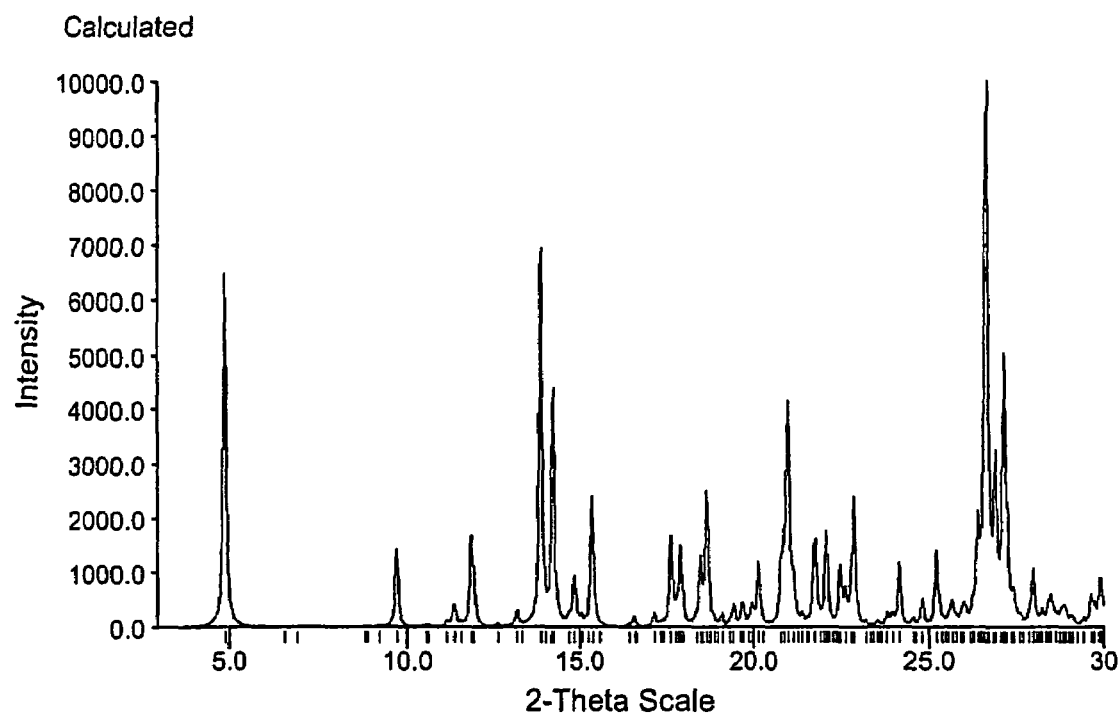
Figure 2A:
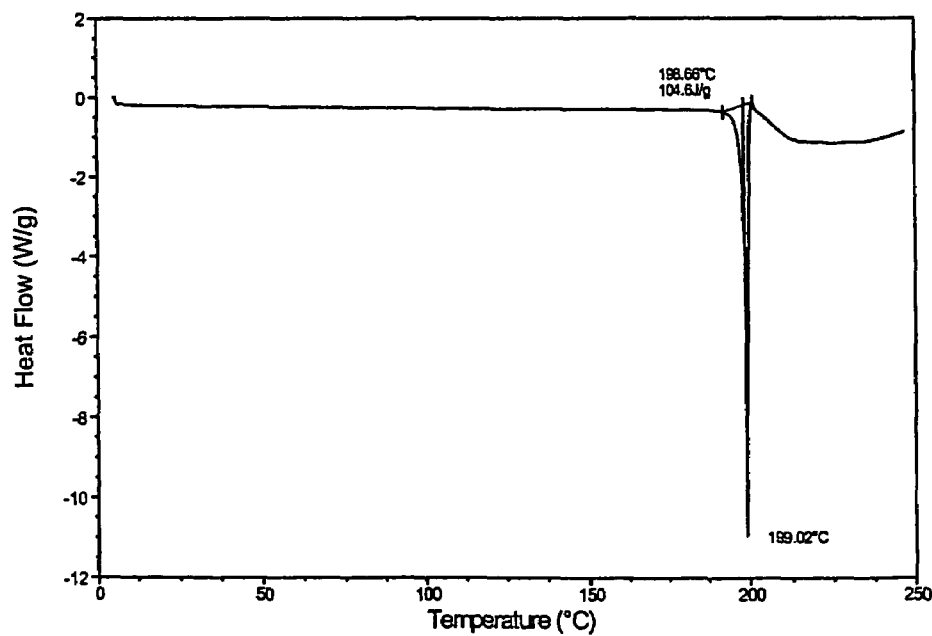
FIGS. 2A and 2B provide the differential scanning calorimetry (DSC) and thermal gravimetric analysis (TGA) data, respectively, of the maleate salt of Formula II.
Figure 2B:
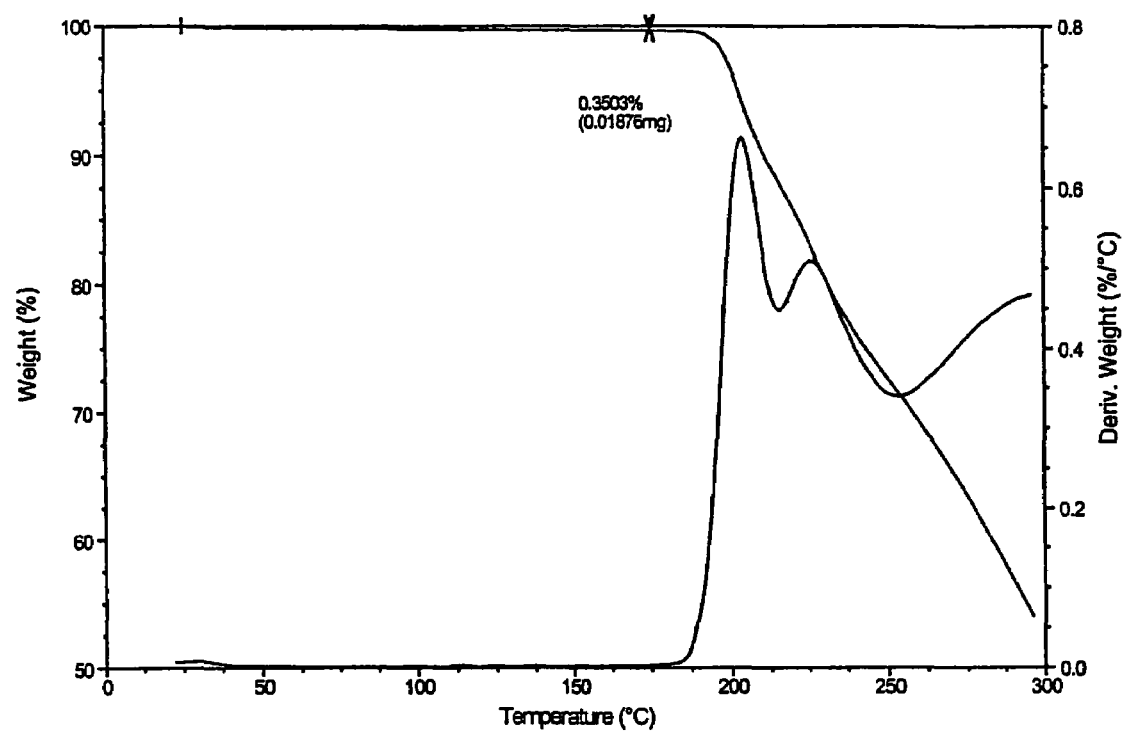
Figure 3:
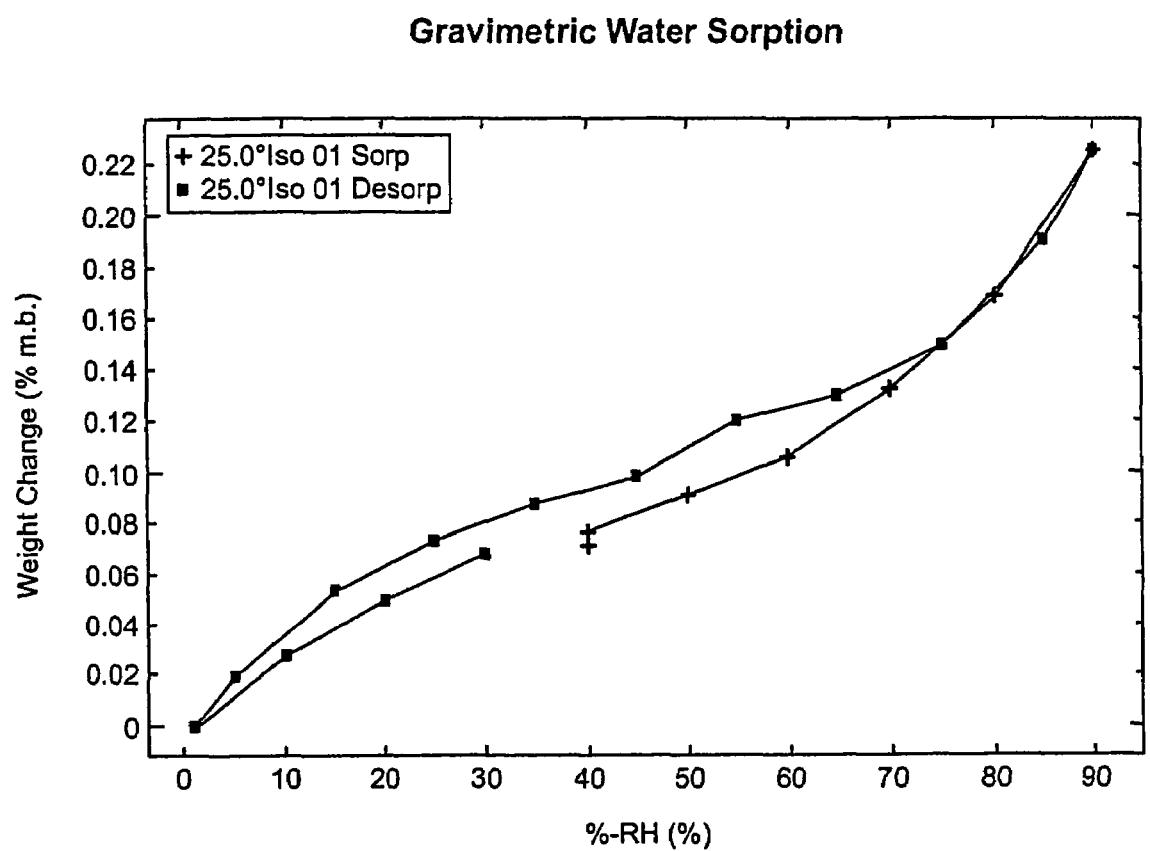
FIG. 3 provides the gravimetric water sorption (GVS) data of the maleate salt of Formula II.
Figure 4:
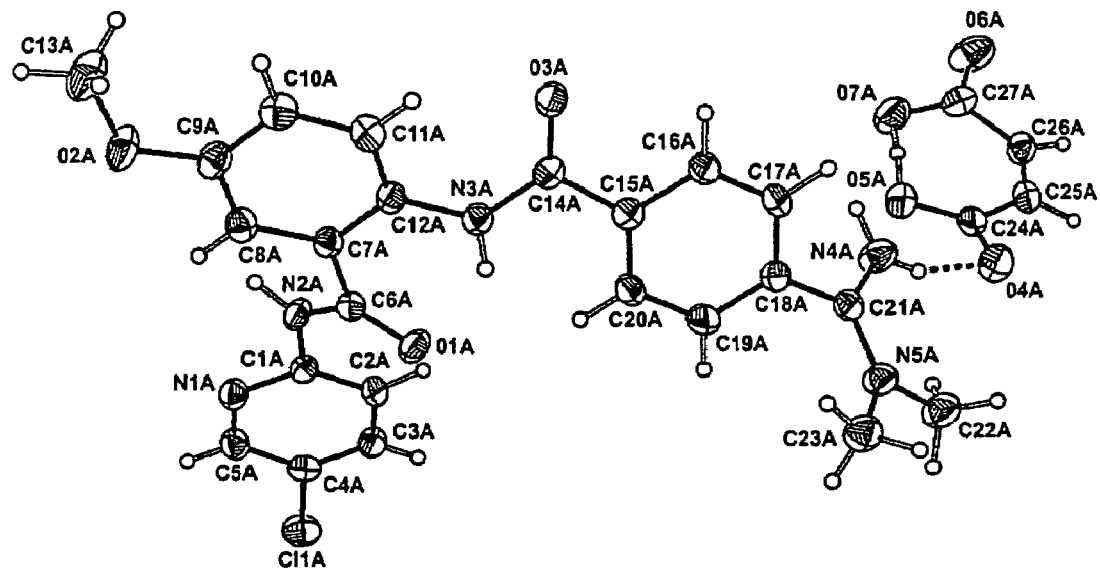
FIG. 4 provides two views of a molecule of the maleate salt of Formula II from the crystal structure data showing the numbering scheme employed. Anisotropic atomic displacement ellipsoids for the non-hydrogen atoms are shown at the 50% probability level. Hydrogen atoms are displayed with an arbitrarily small radius.
Figure 4:
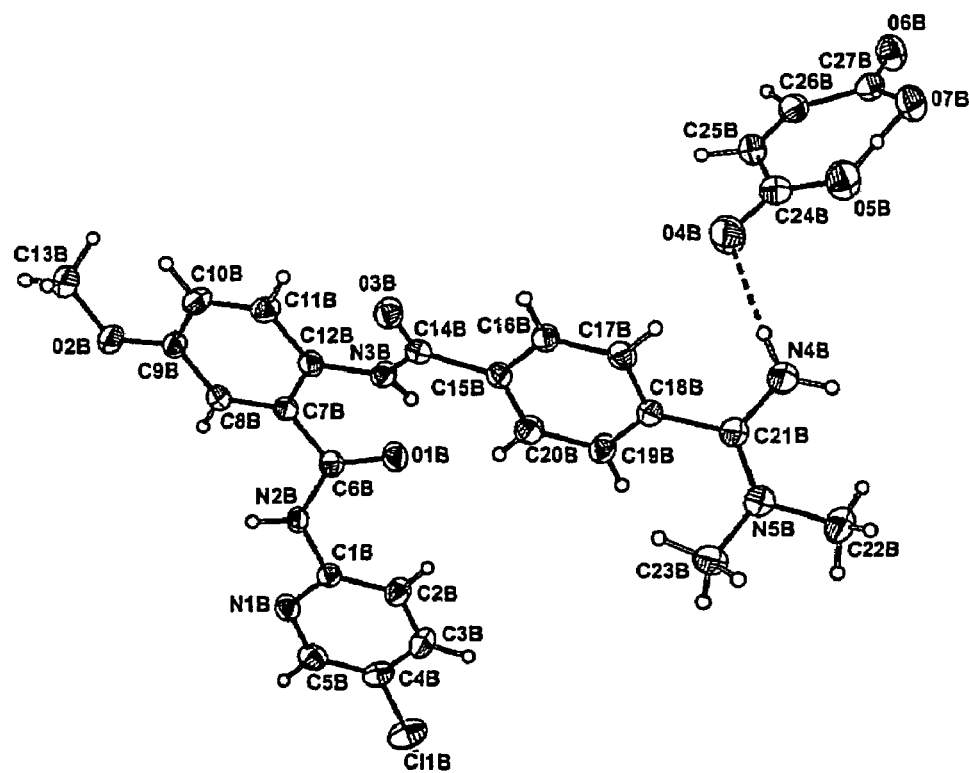

The salt of Formula II was characterized using the techniques described in Example 4. The X-ray diffraction pattern for the salt of Formula II is shown in FIG. 1A, and is characterized by the following approximate peak locations: 4.9, 9.7, 11.8, 13.8, 14.1, 15.2, 17.6, 18.5, 19.9, 20.8, 21.6, 22.7, 24.1, 25.0, 26.3, 26.8 degrees 2θ. A melting point of between 197 and 201° C. was measured using differential scanning calorimetry (DSC, see pattern in FIG. 2A). In addition, a weight loss of 0.62% at 100° C. of the salt of Formula II was measured via thermal gravimetric analysis (TGA, see pattern in FIG. 2B). Water sorption of the salt of Formula II was reversible and showed a water uptake of between 0.1 and 3% (FIG. 3). Purity of the salt of Formula II was measured by the presence of hydrolyzed amidine content as measured by HPLC, and the purity was found to be >99%.

$^1$H NMR (DMSO-$d_6$): δ 3.0 (s, 3H), 3.2 (s, 3H), 3.82 (s, 3H), 7.2 (d, 1H, J=9.0 Hz), 7.42 (s, 1H), 7.68 (d, 1H, J=8.0 Hz), 7.95-8.15 (m, 2H), 8.12 (m), 8.18(m, 1H), 8.42 (s, 1H), 9.0 (s, 1H), 11.0 (s, 1H), 11.2 (s, 1H); IR (KBr, cm$^{-1}$): 3300, 1685, 1600 1515, 1380, 1270, 1200, 1100, 1050, 880, 800, 710.

Example 2

Preparation of the Compound of Formula I

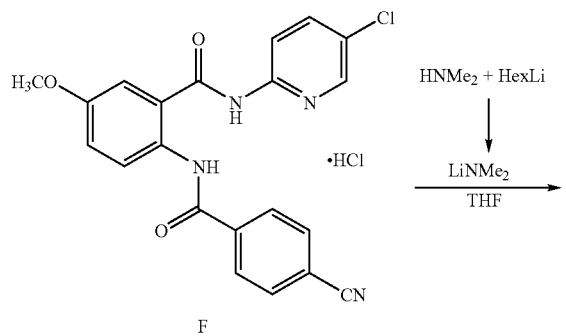

F

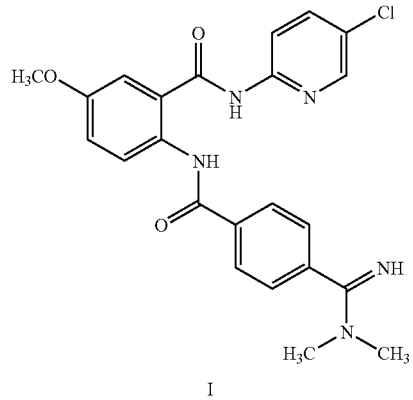

I

Gram Scale Preparation

A slurry of the compound of Formula F (455 g, 1.0 eq.) in THF (4.67 kg, 10.3 parts) was prepared and adjusted to <10° C. Lithium dimethyl amide was prepared as follows; hexyllithium (2.3 N/hexane, 2.45 L, 5.5 eq.) was added to dimethylamine solution (2 N/THF, 2.8 L, 5.5 eq.) maintaining <10° C. The lithium dimethyl amide solution was charged into the slurry containing the compound of Formula F keeping the pot temperature of <10° C. The reaction progress was monitored by in-process HPLC which confirmed that the amount of Formula F was <1.0 A %. A buffer solution of NaHCO$_3$ (490 g, 1.1 parts, 5.7 eq.) and Na$_2$CO$_3$ (490 g, 1.1 parts, 4.5 eq.) in deionized water (6.6 kg, 14.51 parts) was prepared, and above reaction mixture was transferred to this aqueous solution maintaining <5° C. The product precipitated out and the resulting slurry was adjusted to 20° C. over a period of 12 hr. The solid was filtered, and the resulting wet cake was washed with 3.5 kg (7.7 parts) of deionized water. The solid was filtered off using a coarse frit glass bench filter, and rinsed forwarded with cold (0-5° C.) absolute ethanol (628 g, 1.4 parts). The product was dried at 30-35° C. Dry product was obtained in 458 g (73% yield).

Kilogram Scale Preparation

A slurry of the compound of Formula F (31.5 Kg, 1.0 eq) in THF (251 Kg, 8.0 parts) was prepared in a 780 L Hastelloy reactor (Reactor A) and adjusted to 0° C. (−3 to 3° C.). 2 M Dimethylamine in THF (161.0 Kg, 5.0 eq) and THF (63 Kg, 2 parts) were charged into a 1900 L GLMS reactor (Reactor B) and adjusted to 0° C. (−3 to 3° C.) with maximum agitation. Hexyllithium (2.3 M, 97.2 Kg, 4.5 eq) was slowly charged to Reactor B while maintaining a max temperature of 10° C. The pump and lines were rinsed forward to Reactor B with THF (3.2 Kg). The Reactor B contents were adjusted to 0° C. (−3 to 3° C.), then transferred to Reactor A while keeping Reactor A temperature ≦10° C. The Reactor B pump and lines were rinsed forward with THF (31.4 Kg, 1.0 part). The Reactor A contents were adjusted to 0° C. (−3 to 3° C.), and agitated at this temperature until the reaction was complete as verified by HPLC (1-2 hrs). After about 1 hr of agitation, in-process HPLC analysis indicated that 0 A % starting material remained (in-process criteria: max 1 A %). Reactor A contents were adjusted to −5° C. (−8 to −3° C.). In-process cleaning of Reactor B with water was performed. Two previously prepared aqueous solutions [NaHCO$_3$ (35.0 Kg, 1.1 parts) in water (236 Kg, 7.5 parts), and Na$_2$CO$_3$ (35.0 Kg 1.1 parts) in water (236 Kg, 7.5 parts)] were charged to Reactor B and adjusted to −3° C. (0 to 6° C.). Reactor A contents were transferred to Reactor B through an insulated line, maintaining the temperature of Reactor B at −8° C. to a maximum of 5° C. The Reactor A pump and lines were rinsed forward with cold [−5° C. (−8 to −3° C.)] THF (31.4 Kg, 1.0 part). Reactor B contents were adjusted to 22° C. (19 to 25° C.) and agitated for ca. 3 hrs. Slurry formation was visually confirmed, and Reactor B contents were filtered onto a 30" centrifuge fitted with F-16 filter cloth. The Reactor B pump and lines were rinsed forward onto the 30" centrifuge fitted with F-16 filter cloth with drinking water (63 Kg, 2 parts). The wet filter cake (66.5 Kg) was transferred back to Reactor B and submitted to a slurry wash in drinking water (1005 Kg, 32 parts) at 22° C. (19 to 25)° C. for ca. 1 hr. The product was filtered onto the 30" centrifuge (after in-process cleaning and fitting with F-53 filter cloth), and the Reactor B lines and pump were rinsed forward with drinking water (63 Kg, 2 parts). The water rinse was sampled for test by TDS, which was found to be 0.46%. The Reactor B pump, lines and wet filter cake were further rinsed with cold [0° C. (−3 to 3° C.)] ethanol (44 Kg, 1.39 parts). The wet filter cake was dried under vacuum with a maximum temperature of water bath (to heat reactor jacket) of 35° C. In-process LOD was 0% after ca. 24 hrs of drying, and the product was discharged (24.8 Kg) in 76.7% yield. HPLC showed 98% purity, with dechlorinated impurity at 1.14%.

Example 3

Preparation of the Compound of Formula F

Step 1. Synthesis of 2-nitro-N-(5-chloro-pyridin-2-yl)-5-methoxy-benzamide (C)

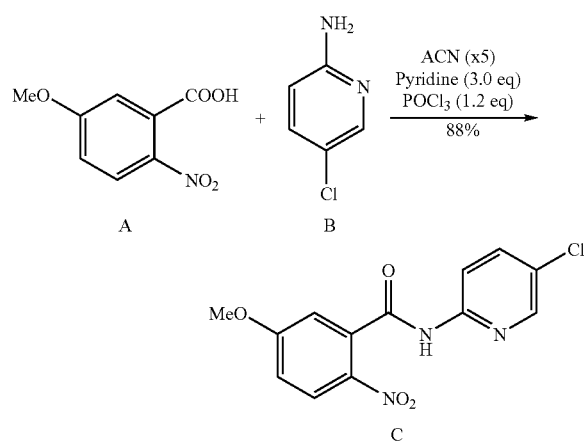

5-Methoxy-2-nitrobenzoic acid (A) (25.0 Kg, 1.0 eq), 2-amino-5-chloropyridine (B) (16.3 Kg, 1.0 eq), and acetonitrile (87.5 Kg, 3.5 parts) were charged to a 380 L GLMS reactor. The reaction mixture was adjusted to 22° C. (19 to 25° C.) and anhydrous pyridine (30.0 Kg, 3.0 eq) was added. The pump and lines were rinsed forward with acetonitrile (22.5 Kg, 0.9 parts), and the reactor contents were adjusted to a temperature of 19-22° C. Phosphorous oxychloride (23.3 Kg, 1.20 eq) was charged to the contents of the reactor via a metering pump, while maintaining a temperature of 25° C. (22-28° C.). The metering pump and lines were rinsed forward with acetonitrile (12.5 Kg, 0.5 parts), while keeping the temperature at 25° C. (22-28° C.). The reaction mixture normally turned from a slurry to a clear solution after the addition of about ⅓ of the POCl₃. At the end of the addition, it became turbid. After complete addition, the reaction mixture was agitated at 25° C. (22-28° C.) for ca. 1 hr, at which time HPLC analysis confirmed reaction completion. The solution was cooled to 15° C. (12-18° C.) and drinking water (156.3 Kg, 6.25 parts) was charged slowly while keeping reaction temperature between 12 and 30° C. The reaction mixture was then adjusted to 22° C. (19 to 25° C.) and agitated for ca. 5 hrs until exotherm ceased. Formation of a slurry was visually confirmed and the contents of the reactor were filtered onto a pressure nutsche fitted with F-19 filter cloth. The reactor, pump, and lines were washed forward onto the pressure nutsche with two portions of drinking water (62.5 Kg, 2.5 parts each). The filtrate had a pH value of 7. The product (41.8 Kg) was dried under vacuum with a maximum temperature of water bath (to heat reactor jacket) of 50° C. After ca. 12 hrs, in-process LOD analysis indicated a solvent content of 0.72%. The dry product (C) was discharged (34.4 Kg) with 88.2% yield and 99.1% purity by HPLC.

Step 2. Synthesis of 2-amino-N-(5-chloro-pyridin-2-yl)-5-methoxy-benzamide (D)

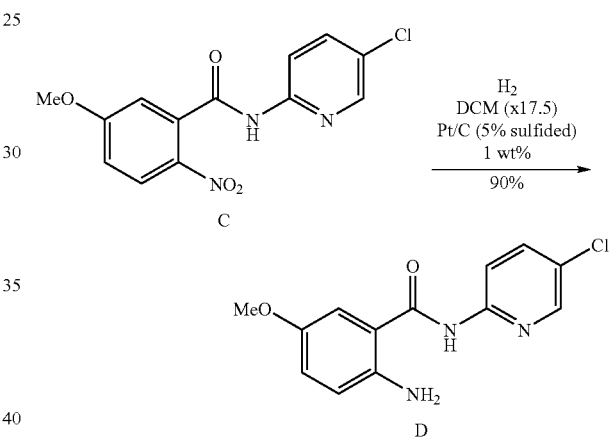

To a 780 L Hastelloy reactor, compound C (33 Kg, 1.0 eq), 5% platinum carbon (sulfided, 0.33 Kg, 0.010 parts) and dichloromethane (578 Kg, 17.5 parts) were charged. Agitation was started and reactor contents were adjusted to 22° C. (19 to 25° C.). The reactor was pressurized with ca. 30 psi hydrogen and the reaction mixture gently heated to 28° C. (25-31° C.). Hydrogenation of the reactor contents was performed under ca. 30 psi at 28° C. (25 to 31° C.; maximum 31° C.) until the reaction was complete by HPLC. After 16.5 hrs, the reaction was deemed complete after confirming the disappearance of starting material (0.472 A %). The contents of the reactor were circulated through a conditioned celite pad (0.2-0.5 Kg celite conditioned with 20-55 Kg dichloromethane) prepared in a 8" sparkler filter to remove the platinum catalyst. The reactor and celite bed were rinsed forward with two portions of dichloromethane (83 Kg, 2.5 parts each). The filtrate was transferred to and concentrated in a 570 L GLMS reactor under a atmospheric pressure to ca. 132 L (4 parts volume). Ethanol (69 Kg, 2.1 parts) was charged and concentration continued under atmospheric pressure to ca. 99 L (3 parts volume). In-process NMR indicated that the dichloromethane content was 39%. Ethanol (69 Kg, 2.1 parts) was charged again and concentration continued again to ca. 99 L (3 parts volume). In-process NMR indicated that the dichloromethane content was 5%. The reaction mixture was then adjusted to 3° C. (0 to 6° C.), agitated for ca. 1 hr, and the resulting slurry filtered onto a jacketed pressure nutsche fitted with F-19 filter cloth. The reactor, pump, and lines were rinsed forward with cold [3° C. (0-6° C.)] ethanol (26 Kg, 0.8 parts). The wet filter cake (36.6 Kg) was dried under vacuum at 40-50° C. with a maximum temperature of water bath (to heat reactor jacket) of 50° C. LOD analysis after 12.5 hrs indicated solvent content was at 0.1%. The dry product (D) was discharged (26.4 Kg) in 89.5% yield. HPLC showed 98.4 A % purity, with dechlorinated impurity at 0.083%.

Step 3. Synthesis of N-(5-chloro-pyridin-2-yl)-2-(4-cyano-benzoyl-amino)-5-methoxy-benzamide Hydrochloride (F)

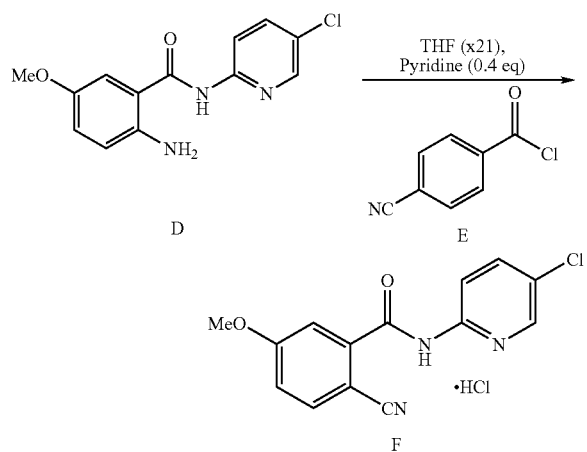

To a 780 L Hastelloy reactor, was charged 4-cyanobenzoyl chloride (E) (17.2 Kg, 1.1 eq) and THF (92 Kg, 3.5 parts). Reactor contents were agitated at 22° C. (19 to 25° C.) until all of the solids had dissolved. The resulting solution was transferred to a lower receiver and the reactor was rinsed forward with THF (26 Kg, 1 part). Compound D (26.4 Kg, 1 eq), THF (396 Kg, 15 parts) and pyridine (2.90 Kg, 0.4 eq) were charged to a clean reactor. The pump and lines were rinsed forward with THF (34 Kg, 1.3 parts). Via a metering pump, the 4-cyanobenzoyl chloride/THF solution was charged to the reactor, keeping the temperature at ≦30° C. and rinsing forward with THF (ca. 10 Kg). The resulting yellow-colored slurry was agitated at 22° C. (19 to 25° C.) for ca 2 hrs. In-process HPLC taken after 2 hrs showed a compound of Formula D content of 0%, indicating completion of the reaction. The slurry was filtered onto a pressure nutsche fitted with F-19 filter cloth. The reactor, pump, lines, and wet cake were rinsed with three portions of ethanol (ca. 15 Kg each). The wet filter cake was discharged (65.4 Kg) and transferred back to the reactor for slurry wash in ethanol (317 Kg, 12 parts) at 22° C. (19 to 25° C.) for ca. 1 hr. The slurry was filtered onto the pressure nutsche and the reactor, pump, lines, and wet filter cake were rinsed with two portions of ethanol (ca. 15 Kg each) and two portions of THF (ca. 15 Kg each). The wet filter cake was dried under vacuum with a maximum temperature of warm glycol bath (to heat the reactor jacket) of 40° C. After 14.5 hrs of drying, LOD was 0.75%. The dried material was milled (screen 0.125") to give 31.8 Kg of product, which was dried under vacuum for another 10.5 hrs. LOD after drying was 1.8%, and the product was discharged (31.5 Kg) in 74.8% yield (expected 60-90%). HPLC showed 100% purity.

Example 4

Salt Screens

Primary Screen

To 20 mg of the free base in 3 mL of 10% (aq.) THF mixture was added 1.1 eq. of the acid in 1 mL ethanol. The mixture was shaken for 2 hours, followed by the addition of 2 mL of tert-butyl methyl ether in order to induce precipitation and shaken for another 2 hours. The samples were then filtered, dried and then analyzed to judge their purity, crystallinity and stability. The results are presented in Table 1 below and list the acid tested.

TABLE 1

| Acid | Salt |
| --- | --- |
| Hydrochloric | +++ |
| Lactic | +++ |
| Maleic | +++ |
| Phenoxyacetic | +++ |
| Propionic | +++ |
| Succinic | +++ |
| Adipic | ++ |
| Ascorbic | ++ |
| Camphoric | ++ |
| Gluconic | ++ |
| Phosphic | ++ |
| Tartric | ++ |
| Citric | ++ |
| Methanesulfonic | ++ |
| Fumaric | + |
| Glycolic | + |
| Naphthalene-1,5-disulfonic | + |
| Gentisic | + |
| Benzene sulfonic | + |
| Camphor sulfonic | − |
| α-Hydroxycaproic | − |
| Benzoic | − |
| Glucuronic | − |
| Ketoglutaric | − |
| Malonic | − |
| Mandelic | − |
| Pyroglutamic | − |
| Sulfuric | − |
| trans-Cinnamic | − |

+++, crystalline form, no phase change, good purity;
++, amorphous, some phase change, moderate to good purity;
+, little or no crystallinity, phase change to less crystalline form, low purity;
−, no precipitation Secondary Screen A secondary evaluation of several salt forms was carried out using the methods described below with the results summarized in the Table 5 and FIGS. 1A, 1B, 2A, 2B and 3.

Differential Scanning Calorimetry (DSC)

DSC data were collected on a TA instrument Q1000 equipped with a 50 position autosampler. The energy and temperature calibration standard was indium. Samples were heated at a rate of 10° C./min between 25 and 350° C. A nitrogen purge at 30 mL/min was maintained over the sample. Between 1 and 3 mg of sample was used, unless otherwise stated, and all samples were crimped in a hermetically sealed aluminium pan.

Thermogravimetric Analysis (TGA)

TGA data were collected on a TA Instrument Q500 TGA, calibrated with Nickel/Alumel and running at scan rates of 10° C./minute. A nitrogen purge at 60 mL/min was maintained over the sample. Typically 10-20 mg of sample was loaded onto a pre-tared platinum crucible.

XRPD (X-Ray Powder Diffraction)

X-Ray Powder Diffraction patterns were collected on a Siemens D5000 diffractometer using CuKα radiation (40 kV, 40 mA), θ-θ goniometer, automatic divergence and receiving slits, a graphite secondary monochromator and a scintillation counter. The instrument is performance checked using a certified Corundum standard (NIST 1976).

Samples run under ambient conditions were prepared as flat plate specimens using powder. Approximately 35 mg of the sample was gently packed into a cavity cut into polished, zero-background (510) silicon wafer. The sample was rotated in its own plane during analysis. The details of the data collection are given for the method in Table 2 below:

TABLE 2

XRPD Method

| Angular range | 3°-40° 2θ |
|---|---|
| Step size | 0.02° 2θ |
| Count time | 6 seconds/step |
| Divergence slit | V20 |
| Anti-scattering slit | V20 |

Diffraction data are reported using Cu Kα$_1$ (λ=1.5406 Å), after the Kα$_2$ component had been stripped using EVA (evaluation software), the powder patterns were indexed by the ITO method using WIN-INDEX and the raw lattice constants refined using WIN-METRIC.

Single Crystal XRD (X-ray Diffraction)

Data were collected on a Bruker AXS 1K SMART CCD diffractometer equipped with an Oxford Cryosystems Cryostream cooling device. Structures were solved using either the SHELXS or SHELXD programs and refined with the SHELXL program as part of the Bruker AXS SHELXTL suite. Unless otherwise stated, hydrogen atoms attached to carbon were placed geometrically and allowed to refine with a riding isotropic displacement parameter. Hydrogen atoms attached to a heteroatom were located in a difference Fourier synthesis and were allowed to refine freely with an isotropic displacement parameter.

Gravimetric Vapour Sorption (GVS) Studies

All samples were run on a Hiden IGASorp moisture sorption analyzer running CFRSorp software. Sample sizes were typically 10 mg. A moisture adsorption desorption isotherm was performed as outlined below (2 scans giving 1 complete cycle). All samples were loaded/unloaded at typical room humidity and temperature (40% RH, 25° C.). All samples were analyzed by XRPD post GVS analysis. The standard isotherm was performed at 25° C. at 10% RH intervals over a 0-90% RH range. The salt of formula II showed excellent moisture stability.

Solubility

This was measured by suspending enough salt in 0.25 mL of solvent (water) to give a maximum final concentration of ≧10 mg/mL of the parent free form of the salt. The suspension was equilibrated at 25° C. for 24 hr followed by a pH check and filtration through a glass fibre C 96 well plate. The filtrate was then diluted down 101×. Quantitation was by HPLC with reference to a standard dissolved in DMSO at approx 0.1 mg/mL. Different volumes of the standard, diluted and undiluted tests were injected. The solubility was calculated by integration of the peak area found at the same retention time as the peak maximum in the standard injection. If there was sufficient solid in the filter plate the XRPD was normally checked for phase changes, hydrate formation, amorphization, crystallization, etc.

Acetate salts provided a solubility of ≧10 mg/mL, while the maleate salts provided a solubility of about 2.05 mg/mL to about 2.27 mg/mL.

pKa Determination

This was performed on a Sirius GlpKa instrument with a D-PAS attachment. Measurements were made by UV in aqueous and by potentiometric in methanol and water mixtures at 25° C. The titration media was ionic strength adjusted with 0.15 M KCl. The values found in the methanol and water mixtures were corrected to 0% co-solvent via a Yasuda-Shedlovsky extrapolation. The data was refined using Refinement Pro software version 1.0. Prediction of pKa values was made using ACD pKa prediction software Ver. 8.08. The data for the salt of formula II is presented below in Table 3.

TABLE 3

| Compound | Predicted/Measured | pKa | Assignment |
|---|---|---|---|
| 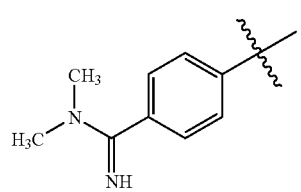 | ACD predicted<br>Measured | 11.91 ± 0.50<br>11.45 | Basic<br>— |
| 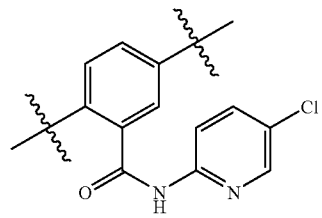 | ACD Predicted<br>Measured | 11.00 ± 0.70<br>10.90 | Acidic<br>— |

TABLE 3-continued

| Compound | Predicted/Measured | pKa | Assignment |
|---|---|---|---|
| 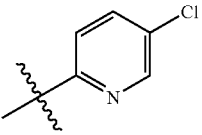 | ACD Predicted<br>Measured | 0.57 ± 0.29<br>1.2 | Basic<br>Basic |

LogP Determination

This was by potentiometric titration on a Sirius GlpKa instrument using three ratios of Octanol:ISA water to generate Log P, Log $P_{ion}$, and Log D values. The data was refined using Refinement Pro software version 1.0. Predictions of LogP were made using ACD Ver. 8.08 and Syracuse KNOW-WIN Ver. 1.67 software. The data for the maleate salt is shown in Table 4 below.

TABLE 4

|  | LogP |
|---|---|
| ACD Predicted LogP | 2.93 |
| Syracuse Predicted LogP | 3.86 |
| Measured LogP | 3.09 |
| Measured LogP$_{ion}$ | −0.08 |
| Measured LogD | 0.09 |

Karl Fisher Water Determination

Water contents were measured on a Mettler Toledo DL39 Coulometer using Hydranal Coulomat AG reagent and an Argon purge. Samples were introduced into the vessel as solids weighed out onto a platinum TGA pan which was connected to a subaseal to avoid water ingress. Approximately 10 mg of sample was used per titration and each analysis was performed in duplicate.

Stability

As a measure of the stability, the hydrolyzed amidine content was measured by HPLC (Agilent HP1100) (retention time of 34 minutes) after subjecting the sample to a temperature of 57° C. with 75% room humidity. The sample solvent was methanol and a mobile phase modifier of 0.1% trifluoroacetic acid was employed. Data were collected after 3, 6 and 10 days except data for the propionate was collected at 0, 3, and 8 days. The results are presented in Table 5 as a percentage of the acid hydrolysis product, expressed as a percentage of the main peak. All other impurity peaks were disregarded in the calculation

TABLE 5

| Salt | Crystallinity | DSC melting point | Water Sorption | Hydrolyzed Amidine Content (3 days) | Hydrolyzed Amidine Content (6 days) | Hydrolyzed Amidine Content (10 days) |
|---|---|---|---|---|---|---|
| Acetate | crystalline | — | non-reversible, high uptake (40%) | 0.62-1.11% | 2.30-3.56% | 3.61-7.90% |
| HCl salt | amorphous | — | — | — | — | — |
| Succinate | amorphous | — | — | — | — | — |
| Citrate | amorphous | — | — | 2.06% | 2.36% | 2.68% |
| Lactate | part crystalline | multiple events | — | — | — | — |
| Maleate | crystalline | 197-201° C. | reversible, low uptake (0.1-3%) | 0.0% | 0.0% | 0.0% |
| Phenoxyacetate | part crystalline | multiple events | — | — | — | — |
| Propionate | crystalline | 129, 253° C. | reversible, medium uptake (3.1%) | 2.22% | 2.97% | 1.71% |
| Mesylate | crystalline | multiple events | — | — | — | — |
| Pamoate/ Embonate | crystalline | — | — | — | — | — |
| Adipate | part crystalline | multiple events | — | — | — | — |
| Ascorbate | — | — | — | — | — | — |
| Camphorate | crystalline | multiple events | — | — | — | — |

TABLE 5-continued

| Salt | Crystallinity | DSC melting point | Water Sorption | Hydrolyzed Amidine Content (3 days) | Hydrolyzed Amidine Content (6 days) | Hydrolyzed Amidine Content (10 days) |
|---|---|---|---|---|---|---|
| Gluconate | — | — | — | — | — | — |
| Phosphate | part crystalline | multiple events | — | — | — | — |
| Tartrate | amorphous | multiple events | — | — | — | — |

Crystal Data for the Salt of Formula II

All experiments are performed on a Bruker-Nonius Kappa CCD diffractometer equipped with an Oxford Cryosystems Cryostream cooling device Structures are usually solved with either SIR-97 or SHELXS-97 and refined with SHELXL-97. Unless otherwise stated, hydrogen atoms are placed geometrically and allowed to refine with isotropic displacement parameters. The following tables (Table 6 and Table 7) provides crystal data and structure refinement for the salt of Formula II.

TABLE 6

| Empirical formula | $C_{27}H_{26}ClN_5O_7$ |
|---|---|
| Formula weight | 567.98 |
| Temperature | 180(2) K |
| Wavelength | 0.71073 Å |
| Crystal size | 0.35 × 0.23 × 0.12 mm |
| Crystal habit | colorless block |
| Crystal system | Triclinic |
| Space group | P1 |
| Unit cell dimensions | a = 10.3321(2) Å α = 73.1530(10)° |
| | b = 14.0715(3) Å β = 75.4860(10)° |
| | c = 19.5756(5) Å γ = 89.6050(10)° |
| Volume | 2630.34(10) Å³ |
| Z | 4 |

TABLE 7

| Theta range for data collection | 3.53 to 26.37° |
|---|---|
| Coverage of independent reflections | 99.4% |
| Goodness-of-fit on $F^2$ | 1.001 |
| Final R indices | R1 = 0.0542, |
| 7196 data; I > 2σ(I) | wR2 = 0.1329 |

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

What is claimed is:

1. A salt represented by Formula II:

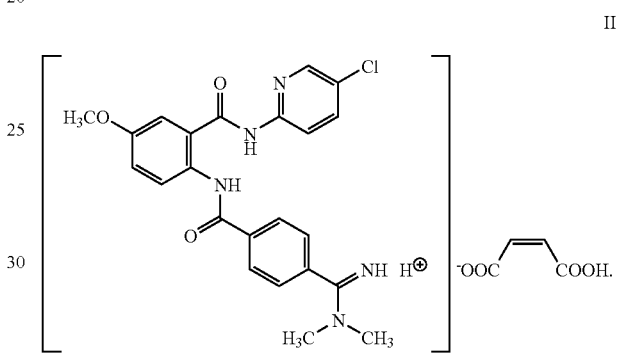

having a crystalline polymorph form.

2. The salt of claim 1, having a powder X-ray diffraction pattern having at least four approximate characteristic peak locations selected from 4.9, 9.7, 13.8, 14.1, 15.2, 17.6, 18.5, 20.8, 21.6, 22.7, 24.1, 26.3, 26.8 degrees 2θ.

3. The salt of claim 1, having a powder X-ray diffraction pattern having at least eight approximate characteristic peak locations selected from 4.9, 9.7, 11.8, 13.8, 14.1, 15.2, 17.6, 18.5, 19.9, 20.8, 21.6, 22.7, 24.1, 25.0, 26.3, 26.8 degrees 2θ.

4. The salt of claim 1, having a powder X-ray diffraction pattern approximate to the powder X-ray diffraction pattern shown in FIG. 1.

5. The salt of claim 1, having a differential scanning calorimetry approximate to the differential scanning calorimetry pattern shown in FIG. 2.

* * * * *